US007902140B1

(12) United States Patent
Hansen

(10) Patent No.: US 7,902,140 B1
(45) Date of Patent: Mar. 8, 2011

(54) CARPET CLEANING WITH FUNGICIDE

(75) Inventor: Eric J. Hansen, Ada, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 1083 days.

(21) Appl. No.: 10/904,054

(22) Filed: Oct. 21, 2004

Related U.S. Application Data

(60) Provisional application No. 60/481,532, filed on Oct. 21, 2003.

(51) Int. Cl.
*A61L 9/00* (2006.01)

(52) U.S. Cl. ......... 510/278; 510/384; 510/426; 510/475; 510/480

(58) Field of Classification Search .................. 510/278, 510/475, 384, 426, 480
See application file for complete search history.

(56) References Cited

U.S. PATENT DOCUMENTS

| | | | | |
|---|---|---|---|---|
| 3,240,710 | A * | 3/1966 | Schiltz | 510/319 |
| 3,775,052 | A | 11/1973 | Van Paassen | |
| 4,587,123 | A * | 5/1986 | Price | 424/405 |
| 4,780,100 | A * | 10/1988 | Moll | 8/137 |
| 5,403,844 | A * | 4/1995 | Mittermeier et al. | 514/275 |
| 5,468,492 | A * | 11/1995 | Szaloki et al. | 424/752 |
| 5,585,407 | A | 12/1996 | Patel et al. | |
| 5,610,189 | A * | 3/1997 | Whiteley | 514/557 |
| 5,872,090 | A * | 2/1999 | You et al. | 510/284 |
| 5,880,076 | A * | 3/1999 | Vermeer | 510/123 |
| 5,905,066 | A * | 5/1999 | Zocchi et al. | 510/280 |
| 5,906,825 | A * | 5/1999 | Seabrook et al. | 424/404 |
| 5,928,384 | A * | 7/1999 | Scialla et al. | 8/137 |
| 5,942,482 | A | 8/1999 | Zocchi et al. | |
| 5,955,413 | A | 9/1999 | Campagna et al. | |
| 6,019,963 | A * | 2/2000 | Kling et al. | 424/76.1 |
| 6,361,787 | B1 | 3/2002 | Shaheen et al. | |
| 6,376,542 | B1 | 4/2002 | Hansen et al. | |
| 6,551,628 | B1 * | 4/2003 | Watson et al. | 424/725 |
| 6,559,189 | B2 * | 5/2003 | Baker et al. | 514/642 |
| 7,470,652 | B2 | 12/2008 | Kilkenny et al. | |
| 2002/0045667 | A1 * | 4/2002 | Baker et al. | 514/642 |
| 2002/0054858 | A1 * | 5/2002 | Lesky et al. | 424/58 |
| 2003/0003140 | A1 * | 1/2003 | Domb et al. | 424/449 |
| 2003/0100465 | A1 * | 5/2003 | Kilkenny et al. | 510/384 |
| 2003/0191034 | A1 * | 10/2003 | Woo et al. | 510/101 |
| 2004/0266634 | A1 | 12/2004 | Bockmuhl et al. | |
| 2006/0058206 | A1 | 3/2006 | Wall et al. | |

FOREIGN PATENT DOCUMENTS

| | | | |
|---|---|---|---|
| DE | 19821106 | * | 5/1998 |
| GB | 2363704 | A | 9/2002 |
| JP | 2002212877 | A | 7/2002 |
| WO | WO 01/16266 | | 3/2001 |
| WO | WO 01/68091 | | 9/2001 |
| WO | 2005087244 | A1 | 9/2005 |

* cited by examiner

*Primary Examiner* — Milton I Cano
*Assistant Examiner* — M. Reza Asdjodi
(74) *Attorney, Agent, or Firm* — McGarry Bair PC

(57) ABSTRACT

A carpet cleaning composition including a fungicide to prevent the growth of fungi on a carpeted surface during an extraction process, particularly during a dry-down period after extraction process wherein residual carpet cleaning solution remains on the carpeted surface. The fungicide is active while the composition is in the liquid state and becomes inactive and friable when the composition is dry. The fungicide bonds to a film that is formed on the carpet fibers to prevent fungi growth on the film. A method of extraction carpet cleaning comprises the steps of depositing the carpet cleaning composition on the carpet, extracting a portion of the cleaning composition with suction leaving on at least some of the carpet fibers an aqueous film that includes the fungicide, and drying the film.

17 Claims, No Drawings

CARPET CLEANING WITH FUNGICIDE

CROSS REFERENCE TO RELATED APPLICATION

This application claims the benefit of U.S. Patent Application Ser. No. 60/481,532, filed Oct. 21, 2003, which is incorporated herein by reference in its entirety.

FIELD OF THE INVENTION

The invention relates to a carpet cleaning. In one of its aspects, the invention relates to a carpet cleaning composition that will prevent the growth of fungi during the extraction process. In another of its aspects, the invention relates to a process of extraction carpet cleaning with reduction of fungi growth during the cleaning process.

DESCRIPTION OF THE RELATED ART

During wet carpet cleaning processes, an extractor, usually equipped with an aqueous cleaning solution storage and delivery system, an agitation system, and a dirty cleaning solution recovery system, applies a cleaning solution to a carpeted surface, agitates the surface to loosen dirt trapped within and between the carpet fibers, and suctions most of the dirty cleaning solution from the carpeted surface. Any cleaning solution remaining on the carpeted surface air-dries during the dry-down period after extraction cleaning. Known carpet cleaning compositions are disclosed in the Campagna et al. U.S. Pat. No. 5,955,413, Scialla et al. U.S. Pat. No. 5,928,384, and the Hansen et al U.S. Pat. No. 6,376,542, all of which are incorporated herein by reference in their entirety. Examples of commercially available cleaning solutions include: BISSELL Fiber Cleansing Formula, Hoover Steam Vac carpet/upholstery detergent, Dirt Devil carpet & rug shampoo, Rug Doctor Steam Cleaner, and Full Release Professional Carpet Cleaner by Oreck.

The dampness remaining in the carpet and carpet backing during the relatively short dry-down period creates an environment potentially susceptible for fungus growth. Unfortunately, fungus may trigger allergic reactions in a relatively small percentage of hypersensitive people. Once a fungus is present, resides in the carpet and reproduces until the environmental conditions are changed or the fungus is physically removed. To avoid fungus growth, allergists sometimes recommend avoiding wet carpet cleaning in those areas inhabited by hypersensitive people. One approach to reduce fungus growth in carpet is to incorporate fungicide into the carpet backing during the mill process. Another approach is a post-installation topical treatment on a periodic basis, for example every six months, or after a major event, such as a flood. While these approaches are suitable for long-term fungus protection, they are not directed to the problem of potential fungus growth during relatively short dry-down period of the wet extraction processes. Furthermore, these approaches require registration by the Environmental Protection Agency (EPA).

SUMMARY OF THE INVENTION

An aqueous carpet cleaning composition comprises water, at least one surfactant, at least one solvent, a chelating agent and optionally, a fragrance, and at least one fungicide that is effective for substantially only that period of time that the composition is in liquid form and no fungicides that are effectice for that period of time when the composition is dry. The fungicide is derived from a natural oil selected from the group consisting of amole lily, California bayberry, California mugwort, camphorweed, desert willow, epazote, labrador tea, oxeye daisy, red cedar, stillingia, sweet root, trumpet creeper and yerba mansa extracts.

In one embodiment, the fungicide is volatile and vaporizes as the composition dries. According to another embodiment, the fungicide is degradable upon drying of the composition.

Further according to the invention, an aqueous carpet cleaning composition comprises water, at least one surfactant, at least one solvent, a chelating agent and optionally, a fragrance and at least one fungicide that is volatile and vaporizes as the composition dries and no other fungicides. The fungicide is derived from a natural oil selected from the group consisting of amole lily, California bayberry, California mugwort, camphorweed, desert willow, epazote, labrador tea, oxeye daisy, red cedar, stillingia, sweet root, trumpet creeper and verba mansa extracts.

In one embodiment, the fungicide is present in the amount of about 0.1 to 5 weight parts/100 weight parts of composition, the surfactant is present in the amount of about 1 to 10 weight parts/100 weight parts of composition and the solvent is present in the amount of about 0.1 to 5 weight parts/100 weight parts of composition. Preferably, the fungicide is present in the amount of about 3 weight parts/100 weight parts of composition, and the surfactant is present in the amount of about 3 weight parts/100 weight parts of composition.

In one embodiment, the surfactant is a non-ionic surfactant and is present in an amount of 0.1 to 2.0 by weight, the solvent is present in an amount of 0.5 to 1.5 by weight and is selected from the group consisting of de-ionized water, glycol ether and terpenes, the chelating agent is present in the amount of 0.1 to 5.0 by weight, and the pH of the composition ranges from 4 to 12 and preferably between 7.5 and 10.

DESCRIPTION OF THE PREFERRED EMBODIMENT

The invention addresses the deficiencies of the prior art by providing a carpet cleaning composition with a fungicide that prevents growth of allergenic fungi during a carpet extraction process. A carpet extraction process involves applying a cleaning solution to a carpeted surface, agitating the surface to loosen dirt trapped within and between the carpet fibers, and suctioning most of the dirty cleaning solution from the carpeted surface. The solution remaining on the carpeted surface is left to air dry during a dry-down period. Any common extractor can be used for the extraction process. An example of a suitable extractor that can be used to apply the carpet cleaning solution to the floor is disclosed in the U.S. Pat. No. 6,131,237 to Kasper, et al.

The fungicide is applied to the carpeted surface as a component of the composition for the carpet cleaning solution during the extraction process and remains active while the solution is in a liquid state. A film forms over the carpeted surface to cover the carpet fibers, and the fungicide bonds with the film. While active, the fungicide can kill existing fungi, prevent reproduction of fungi, and prevent growth of fungi on the film. The solution remains in a liquid state from the time it is applied to the carpeted surface until it is either removed by extraction or, if not removed, dried on the surface. Once the carpet cleaning solution dries, the fungicide becomes inactive. The fungicide cannot be oily or leave an oily residue on the carpeted surface after the carpet cleaning solution dries. Further, the fungicide preferably becomes friable upon drying and can thereafter be removed by vacuuming, if desired.

The carpet cleaning composition includes common carpet cleaning solution ingredients and at least one fungicide. The common carpet cleaning solution ingredients include, but are not limited to, deioinzed water, at least one surfactant, at least one solvent, a fragrance, and a chelating agent. Examples of common carpet cleaning ingredients are given in the pending U.S. patent application Ser. No. 10/604,780, now publication US2004063600, which is incorporated herein by reference in its entirety.

The at least one fungicide can be selected from many synthetic or natural fungicides to inhibit fungus growth during the dry-down period. Natural fungicides are preferred because of the relatively short efficacy period as compared to synthetic fungicides. Natural fungicides achieve shorter efficacy periods due to their volatile characteristics and their tendency to degrade after dry-down. The preferred natural fungicides are derived from natural oils and include tea tree and grapefruit extract. Other suitable natural oil fungicides are *Aloe*, Amole Lily (scalp), Ash, Balsamroot, *Calendula*, California Bay Laurel, California Bayberry, California Mugwort, Camphorweed, Candidiasis, Chaparral, Cypress, Desert Willow, *Echinacea*, Epazote, *Eucalyptus* (upper GI), Labrador Tea, Oregon Grape, Oxeye Daisy, Red Cedar, Stillingia, Sweet Root, Trumpet Creeper, White Sage, and Yerba Mansa.

Synthetic fungicides can also be used in the invention and are advantageous because they can be used at lower levels that the natural fungicides, and therefore are more cost effective. Further, they can be chemically modified to target specific fungi and they exhibit specified volatility and degradation characteristics. Suitable synthetic fungicides can be selected from the following groups:

ALIPHATIC NITROGEN FUNGICIDES including butylamine, cymoxanil, dodicin, dodine, guazatine, and iminoctadine.

AMIDE FUNGICIDES including, carpropamid, chloraniformethan, cyazofamid, cyflufenamid, diclocymet, ethaboxam, fenoxanil, flumetover, furametpyr, prochloraz, quinazamid, silthiofam, and triforine.

ACYLAMINO ACID FUNGICIDES including benalaxyl, benalaxyl-M, furalaxyl, metalaxyl, metalaxyl-M, pefurazoate; benzamide fungicides such as benzohydroxamic acid, tioxymid, trichlamide, zarilamid and zoxamide; furamide fungicides such as, cyclafuramid and furmecyclox; phenylsulfamide fungicides such as dichlofluanid, tolylfluanid; valinamide fungicides such as benthiavalicarb, iprovalicarb; anilide fungicides such as benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide, tiadinil; benzanilide fungicides such as benodanil, flutolanil, mebenil, mepronil, salicylanilide, tecloftalam; furanilide fungicides such as fenfuram, furalaxyl, furcarbanil, methfuroxam, and sulfonanilide fungicides such as flusulfamide.

ANTIBIOTIC FUNGICIDES including aureofungin, blasticidin-S, cycloheximide, griseofulvin, kasugamycin, natamycin, polyoxins, polyoxorim, streptomycin, validamycin; strobilurin fungicides such as azoxystrobin, dimoxystrobin, fluoxastrobin, kresoxim-methyl, metominostrobin, orysastrobin, picoxystrobin, pyraclostrobin and trifloxystrobin.

AROMATIC FUNGICIDES including biphenyl, chlorodinitronaphthalene, chloroneb, chlorothalonil, cresol, dicloran, hexachlorobenzene, pentachlorophenol, quintozene, sodium pentachlorophenoxide, and tecnazene.

BENZIMIDAZOLE FUNGICIDES including benomyl, carbendazim, chlorfenazole, cypendazole, debacarb, fuberidazole, mecarbinzid, rabenzazole, and thiabendazole.

BENZIMIDAZOLE PRECURSOR FUNGICIDES including furophanate, thiophanate and thiophanate-methyl.

BENZOTHIAZOLE FUNGICIDES including bentaluron, chlobenthiazone, and TCMTB.

BRIDGED DIPHENYL FUNGICIDES including bithionol, dichlorophen, and diphenylamine.

CARBAMATE FUNGICIDES including benthiavalicarb, furophanate, iprovalicarb, propamocarb, thiophanate, thiophanate-methyl; benzimidazolylcarbamate fungicides such as benomyl, carbendazim, cypendazole, debacarb, mecarbinzid; and carbanilate fungicides such as diethofencarb.

CONAZOLE FUNGICIDES including conazole fungicides (imidazoles) such as climbazole, clotrimazole, imazalil oxpoconazole, prochloraz, triflumizole; conazole fungicides (triazoles) such as azaconazole, bromuconazole, cyproconazole, diclobutrazol, difenoconazole, diniconazole or diniconazole-M, epoxiconazole, etaconazole, fenbuconazole, fluquinconazole, flusilazole, flutriafol, furconazole or furconazole-cis, hexaconazole, imibenconazole, ipconazole metconazole, myclobutanil, penconazole, propiconazole, prothioconazole, quinconazole, simeconazole, tebuconazole, tetraconazole, triadimefon, triadimenol, triticonazole, uniconazole or uniconazole-P.

COPPER FUNGICIDES including bordeaux mixture, burgundy mixture, chestnut mixture, copper acetate, copper carbonate, basic, copper hydroxide, copper naphthenate, copper oleate, copper oxychloride, copper sulfate, copper sulfate, basic, copper zinc, cromate, cufraneb, cuprobam, cuprous oxide, mancopper, and oxine copper.

DICARBOXIMIDE FUNGICIDES including famoxadone, fluoroimide, dichlorophenyl dicarboximide fungicides such as chlozolinate, dichlozoline, iprodione, isovaledione, myclozolin, procymidone, vinclozolin; phthalimide fungicides such as, captafol, captan, ditalimfos, folpet, and thiochlorfenphim.

DINITROPHENOL FUNGICIDES including binapacryl, dinobuton, dinocap or dinocap-4 or dinocap-6, dinocton, dinopenton, dinosulfon, dinoterbon, DNOC.

DITHIOCARBAMATE FUNGICIDES including azithiram, carbamorph, cufraneb, cuprobam, disulfiram, ferbam, metam, nabam, tecoram, thiram, ziram; cyclic dithiocarbamate fungicides such as dazomet, etem, milneb; polymeric dithiocarbamate fungicides such as mancopper, mancozeb, maneb, metiram, polycarbamate, propineb, and zineb.

IMIDAZOLE FUNGICIDES including cyazofamid, fenamidone, fenapanil, glyodin, iprodione, isovaledione, pefurazoate, and triazoxide.

INORGANIC FUNGICIDES including potassium azide, potassium thiocyanate, sodium azide, and sulfur.

MERCURY FUNGICIDES including inorganic mercury fungicides such as mercuric chloride, mercuric oxide, mercurous chloride; organomercury fungicides such as, (3-ethoxypropyl)mercury bromide, ethylmercury acetate, ethylmercury bromide, ethylmercury chloride, ethylmercury 2,3-dihydroxypropyl mercaptide, ethylmercury phosphate, N-(ethylmercury)-p-toluenesulphonanilide, hydrargaphen, 2-methoxyethylmercury chloride, methylmercury benzoate, methylmercury dicyandiamide, methylmercury pentachlorophenoxide, 8-phenylmercurioxyquinoline, phenylmercuriurea, phenylmercury acetate, phenylmercury chloride, phenylmercury derivative of pyrocatechol, phenylmercury nitrate, phenylmercury salicylate, thiomersal, and tolylmercury acetate.

MORPHOLINE FUNGICIDES including aldimorph, benzamorf, carbamorph, dimethomorph, dodemorph, fenpropimorph, flumorph, and tridemorph.

ORGANOPHOSPHORUS FUNGICIDES including ampropylfos, ditalimfos, edifenphos, fosetyl, hexylthiofos, iprobenfos, phosdiphen, pyrazophos, tolclofos-methyl, and triamiphos.

ORGANOTIN FUNGICIDES including decafentin, fentin, and tributyltin oxide.

OXATHIIN FUNGICIDES including carboxin and oxycarboxin.

OXAZOLE FUNGICIDES including chlozolinate, dichlozoline, drazoxolon, famoxadone, hymexazol, metazoxolon, myclozolin, oxadixyl, and vinclozolin.

POLYSULFIDE FUNGICIDES including barium polysulfide, calcium polysulfide, potassium polysulfide, and sodium polysulfide.

PYRIDINE FUNGICIDES including boscalid, buthiobate, dipyrithione, fluazinam, pyridinitril, pyrifenox, pyroxychlor, and pyroxyfur.

PYRIMIDINE FUNGICIDES including bupirimate, cyprodinil, diflumetorim, dimethirimol, ethirimol, fenarimol, ferimzone, mepanipyrim, nuarimol, pyrimethanil, and triarimol PYRROLE FUNGICIDES including fenpiclonil, fludioxonil, and fluoroimide.

QUINOLINE FUNGICIDES including ethoxyquin, halacrinate, 8-hydroxyquinoline sulfate, quinacetol, and quinoxyfen.

QUINONE FUNGICIDES including benquinox, chloranil, dichlone, and dithianon.

QUINOXALINE FUNGICIDES including chinomethionat, chlorquinox, and thioquinox.

THIAZOLE FUNGICIDES including ethaboxam, etridiazole, metsulfovax, octhilinone, thiabendazole, thiadifluor, and thifluzamide.

THIOCARBAMATE FUNGICIDES including methasulfocarb and prothiocarb.

THIOPHENE FUNGICIDES including ethaboxam and silthiofam.

TRIAZINE FUNGICIDES including anilazine.

TRIAZOLE FUNGICIDES including bitertanol, fluotrimazole, and triazbutil.

UREA FUNGICIDES including bentaluron, pencycuron, and quinazamid.

UNCLASSIFIED FUNGICIDES including acibenzolar, acypetacs, allyl alcohol, benzalkonium chloride, benzamacril, bethoxazin, carvone, chloropicrin, DBCP, dehydroacetic acid, diclomezine, diethyl pyrocarbonate, fenaminosulf, fenitropan, fenpropidin, formaldehyde, hexachlorobutadiene, isoprothiolane, methyl bromide, methyl isothiocyanate, metrafenone, nitrostyrene, nitrothal-isopropyl, OCH, 2-phenylphenol, phthalide, piperalin, probenazole, proquinazid, pyroquilon, sodium orthophenylphenoxide, spiroxamine, sultropen, thicyofen, tricyclazole, and zinc naphthenate.

An example of the relative concentration of the ingredients in the carpet cleaning composition is presented in Table 1.

TABLE 1

Exemplary Carpet Cleaning Composition

| Ingredient | Amount (weight %) | Range (weight %) |
|---|---|---|
| Deionized Water | 85 | 75-98 |
| Surfactant | 3 | 1-10 |
| Solvent | 3 | 0.1-5 |
| Fragrance | 3 | 0.1-5 |
| Chelating Agent | 3 | 0.1-5 |
| Fungicide | 3 | 0.1-5 |

Preferably, the carpet cleaning composition forms a stable mixture or solution with a pH in the range of 4 to 12 and preferably between 7.5 and 10.

The carpet cleaning composition is applied directly to the carpet fibers. During the drying process, the carpet cleaning solution develops a surfactant film over the carpet fibers, and the fungicide bonds with the surfactant film to prevent fungus growth thereon.

The carpet cleaning composition can be manufactured in several forms. For example, a ready-to-use solution can be directly transferred to the extractor, or a concentrated version of the solution can be diluted prior to use in the extractor or can be used in a dual-tank extractor that dilutes the concentrated version during the extraction process. On the other hand, an alternate version of the carpet cleaning composition can be prepared as a fungicide concentrate that can be utilized with other carpet cleaning solutions. Possible delivery systems for the fungicide concentrate include a liquid solution or dissolvable pouches.

By incorporating the fungicide into the carpet cleaning composition, anti-allergy aspects of the extraction process are significantly improved. The carpet cleaning solution prevents proliferation of fungi on the carpeted surface and thereby decreases the likelihood of an asthmatic or allergic reaction instigated by the extraction processes. Furthermore, prevention of fungi growth contributes to an overall cleaner carpet, and the fungicide within the extractor cleaning solution supply and recovery systems can prevent fungal growth in the extractor. Because the fungicide becomes inactive upon drying, potential concerns about active chemicals on the carpeted surface and their effects on the inhabitants, including humans and animals, of the house/building are alleviated. Additionally, the friable fungicide can be easily removed from the carpeted surface by dry vacuuming if desired.

While the invention has been specifically described in connection with certain specific embodiments thereof, it is to be understood that this is by way of illustration and not of limitation. Reasonable variation and modification are possible within the forgoing disclosure and drawings without departing from the spirit of the invention that is defined in the appended claims.

What is claimed is:

1. An aqueous carpet cleaning composition comprising:

water, at least one surfactant, at least one solvent, a chelating agent and optionally, a fragrance;

at least one fungicide that is effective for substantially only that period of time that the composition is in liquid form; and no fungicides that are effective for that period of time when the composition is dry, wherein the fungicide is derived from a natural oil selected from the group consisting of amole lily, California bayberry, California mugwort, camphorweed, desert willow, epazote, labrador tea, oxeye daisy, red cedar, stillingia, sweet root, trumpet creeper, and yerba mansa extracts.

2. An aqueous carpet cleaning composition according to claim 1 wherein the fungicide is volatile and vaporizes as the composition dries.

3. An aqueous carpet cleaning composition according to claim 1 wherein the fungicide is degradable upon drying of the composition.

4. An aqueous carpet cleaning composition according to claim 1 wherein the surfactant is present in an amount of about 0.1 to 2.0 weight parts/100 weight parts of composition and is a non-ionic surfactant.

5. An aqueous carpet cleaning composition according to claim 1 where in the solvent is present in the amount of about 0.5 to 1.5 weight parts/100 weight parts of composition and is selected from the group consisting of de-ionized water, glycol ether and terpenes.

6. An aqueous carpet cleaning composition according to claim 1 where in the chelating agent is present in the amount of about 0.1 to 5.0 weight parts/100 weight parts of composition.

7. An aqueous carpet cleaning composition according to claim 1 wherein the pH of the composition ranges from 4 to 12.

8. An aqueous carpet cleaning composition according to claim 1 wherein the pH of the composition is between 7.5 and 10.

9. An aqueous carpet cleaning composition according to claim 1 wherein the fungicide is present in the amount of about 0.1 to 5 weight parts/100 weight parts of composition.

10. An aqueous carpet cleaning composition according to claim 9 wherein the surfactant is present in the amount of about 1 to 10 weight parts/100 weight parts of composition.

11. An aqueous carpet cleaning composition according to claim 10 wherein the fungicide is present in the amount of about 3 weight parts/100 weight parts of composition, and the surfactant is present in the amount of about 3 weight parts/100 weight parts of composition.

12. An aqueous carpet cleaning composition according to claim 10 wherein the solvent is present in the amount of about 0.1 to 5 weight parts/100 weight parts of composition.

13. An aqueous carpet cleaning composition comprising:

water, at least one surfactant, at least one solvent, a chelating agent and optionally, a fragrance;

at least one fungicide that is volatile and vaporizes as the composition dries; and no other fungicides, wherein the fungicide is derived from a natural oil selected from the group consisting of amole lily, California bayberry, California mugwort, camphorweed, desert willow, epazote, labrador tea, oxeye daisy, red cedar, stillingia, sweet root, trumpet creeper, and yerba mansa extracts.

14. An aqueous carpet cleaning composition according to claim 13 wherein the fungicide is degradable upon drying of the composition.

15. An aqueous carpet cleaning composition according to claim 13 wherein the fungicide is present in the amount of about 0.1 to 5 weight parts/100 weight parts of composition.

16. An aqueous carpet cleaning composition according to claim 15 wherein the surfactant is present in the amount of about 1 to 10 weight parts/100 weight parts of composition.

17. An aqueous carpet cleaning composition according to claim 16 wherein the solvent is present in the amount of about 0.1 to 5 weight parts/100 weight parts of composition.

* * * * *